(12) United States Patent
Reichel et al.

(10) Patent No.: US 11,877,869 B2
(45) Date of Patent: Jan. 23, 2024

(54) METHOD AND SYSTEM FOR DETERMINING A CARBOHYDRATE INTAKE EVENT FROM GLUCOSE MONITORING DATA INDICATIVE OF A GLUCOSE LEVEL, AND A NON-TRANSITORY COMPUTER READABLE MEDIUM

(71) Applicant: Roche Diabetes Care, Inc., Indianapolis, IN (US)

(72) Inventors: Andreas Reichel, Dresden (DE); Tobias Wiesner, Leipzig (DE); Bernd Steiger, Roemerberg (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 1079 days.

(21) Appl. No.: 16/331,577

(22) PCT Filed: Sep. 29, 2017

(86) PCT No.: PCT/EP2017/074774
§ 371 (c)(1),
(2) Date: Mar. 8, 2019

(87) PCT Pub. No.: WO2018/060424
PCT Pub. Date: Apr. 5, 2018

(65) Prior Publication Data
US 2019/0216405 A1     Jul. 18, 2019

(30) Foreign Application Priority Data
Sep. 30, 2016   (EP) .................................... 16191724

(51) Int. Cl.
*A61B 5/00*     (2006.01)
*A61B 5/145*    (2006.01)
(Continued)

(52) U.S. Cl.
CPC ........ *A61B 5/7282* (2013.01); *A61B 5/14532* (2013.01); *A61B 5/4839* (2013.01);
(Continued)

(58) Field of Classification Search
CPC combination set(s) only.
See application file for complete search history.

(56) References Cited

U.S. PATENT DOCUMENTS

| | | |
|---|---|---|
| 2010/0161346 A1 | 6/2010 | Getschmann |
| 2014/0088393 A1 | 3/2014 | Bernstein |

(Continued)

FOREIGN PATENT DOCUMENTS

| | | |
|---|---|---|
| CN | 103702697 | 4/2014 |
| CN | 104081208 | 10/2014 |

(Continued)

OTHER PUBLICATIONS

Dassau, et al.: "Detection of a Meal Using Continuous Glucose Monitoring: Implications for an artificial B-cell", Diabetes Care, vol. 3, issue 2, pp. 295-300.

(Continued)

*Primary Examiner* — Christian Jang
(74) *Attorney, Agent, or Firm* — Woodard, Emhardt, Henry, Reeves & Wagner, LLP

(57) ABSTRACT

The disclosure relates to a method and a system for determining a carbohydrate intake event from glucose monitoring data indicative of a glucose level in a system having a data processing device provided with one or more processors. The method comprises steps of: receiving a glucose monitoring value by the data processing device, the glucose monitoring value indicating a glucose level sampled from a person in a bodily fluid in a glucose level measurement; receiving, by the data processing device, insulin bolus administration data indicating an insulin bolus of an insulin (Continued)

Figure 1:
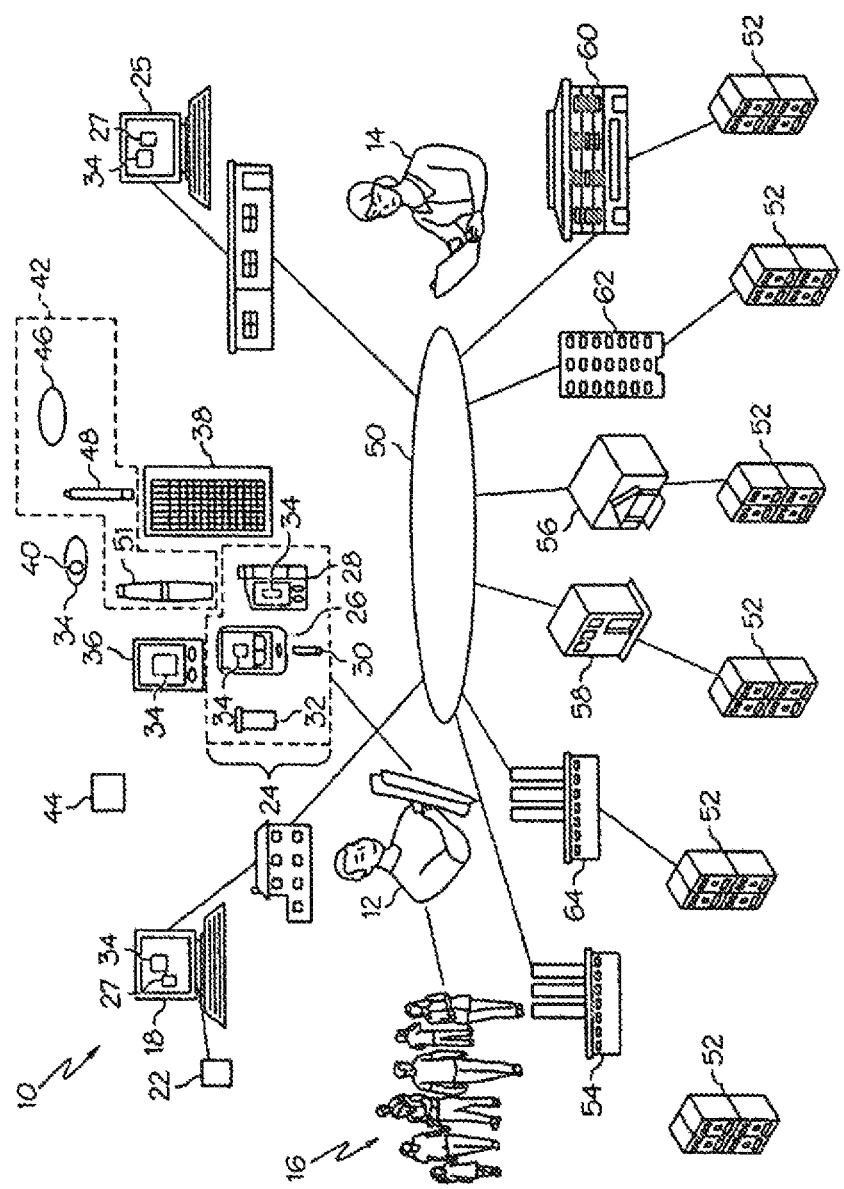

bolus administration; determining, by the data processing device, from an analysis of the glucose monitoring value, a carbohydrate intake event if one of the following is detected: the glucose monitoring value indicates a glucose level below a first threshold glucose level; and the glucose monitoring value indicates an elevated glucose level above a second threshold glucose level, and the insulin bolus indicated by the insulin bolus administration data is exceeding a corrective insulin bolus suitable for compensating for the elevated glucose level; and generating, by the data processing device, carbohydrate intake event data indicating the determined carbohydrate intake event. Further, a non-transitory computer readable medium is provided.

15 Claims, 4 Drawing Sheets

(51) Int. Cl.
*G16H 50/20* (2018.01)
*G16H 20/17* (2018.01)

(52) U.S. Cl.
CPC ............ *A61B 5/4848* (2013.01); *G16H 20/17* (2018.01); *G16H 50/20* (2018.01); *A61B 5/4833* (2013.01); *A61B 5/7475* (2013.01)

(56) References Cited

U.S. PATENT DOCUMENTS

| | | |
|---|---|---|
| 2014/0107607 A1 | 4/2014 | Estes |
| 2015/0190098 A1 | 7/2015 | Patek |
| 2015/0289821 A1 | 10/2015 | Rack-Gomer |

FOREIGN PATENT DOCUMENTS

| | | |
|---|---|---|
| CN | 104520862 | 4/2015 |
| CN | 104620244 | 5/2015 |
| CN | 105899127 | 8/2016 |
| WO | WO 2011016028 | 2/2011 |

OTHER PUBLICATIONS

Niyathapala, et al.: "Nanalysis and Development of a Meal Detection Algorithm for the Artificial Pancreas", retrieved from http://sccur.csuci.edu/abstract/analysis-and-development-of-a-meal-detection-algorithm-for-the-artificial-p on Jun. 2, 2021.

METHOD AND SYSTEM FOR DETERMINING A CARBOHYDRATE INTAKE EVENT FROM GLUCOSE MONITORING DATA INDICATIVE OF A GLUCOSE LEVEL, AND A NON-TRANSITORY COMPUTER READABLE MEDIUM

The present disclosure refers to a method and a system for determining a carbohydrate intake event from glucose monitoring data indicative of a glucose level, and a non-transitory computer readable medium.

BACKGROUND

Glucose monitoring helps people with diabetes manage the disease and avoid its associated problems. A person can use the results of glucose monitoring to make decisions about food, physical activity, and medications. A common way to check glucose level is performing discontinuous monitoring. Such checking usually involves pricking a fingertip with an automatic lancing device to obtain a blood sample and then using a glucose meter to measure the blood sample's glucose level. Such monitoring may also be referred to as spot monitoring.

As an alternative or in addition continuous glucose monitoring (CGM) may be applied. A system for CGM may use a body sensor inserted under the skin to check glucose levels repetitively over its wear time. The sensor stays in place for several days to weeks and then must be replaced. A transmitter sends information about an analyte value or level indicative of the glucose level (e.g., via wireless data transmission) from the sensor to a monitor device. The user may check blood samples with a spot monitoring blood glucose meter to calibrate the devices.

Patients with diabetes may be asked to perform a number of data collections in an effort to diagnose a chronic DC or to optimize therapy. For example, diabetic patients may measure their glucose level concurrently with various events that occur according to the patient's lifestyle such as physical activity, eating and sleeping. The events may or may not be correlated with or influence biomarkers such as glucose level of the chronic DC or the optimization or therapy. However, the correlations between the events and the biomarkers of the chronic DC can be difficult to identify. Methods and systems were proposed for visualizing correlations between glucose data and events.

In order to assess his glycemic situation and to manage the insulin therapy there is a need for a diabetes patient to consider in addition to the measured glucose level other contextual information such as the amount of insulin bolus administered recently and the amount of carbohydrate consumed (e.g. eating a meal) or soon to be consumed. Sometimes patients fail to enter such carbohydrate consumption information into their diabetes management systems which in turn adversely affect the ability to assess glycemic status and to determine whether or not the patient's interventions (insulin bolus, carb intake) are or have been appropriate. As a consequence, it would improve the management of diabetes if the diabetes management system would be able to detect if carbohydrate consumption is likely to have occurred and to inform the patient or request from the patient to enter such data.

Document WO 2014/074338 A1 discloses a diabetes data management system. From an analysis of continuous glucose monitoring values an event may be detected such as a missed meal event. In response to the detected missed meal event the user is prompted to enter meal information.

Further, an insulin delivery system is disclosed in document US 2014/0155679 A1. An automatic meal detection algorithm may be provided that identifies rapid rise time in the glucose level on a continuous glucose level signal.

Document US 2014/0107607 A1 refers to an infusion pump system that can be configured to activate an alarm in response to a calculated prediction of the user's future blood glucose levels. The predictive calculation of the user's future blood glucose levels can be based at least in part upon a recent blood glucose level, a trend of blood glucose levels over time, and an insulin load of the user.

In document US 2014/0088393 A1 a handheld analyte measurement device is disclosed. The analyte measurement device includes one or more software applications to help the user manage their diabetes.

Document US 2015/0190098 A1 refers to an Adaptive Advisory Control (AA Control) interactive process involving algorithm-based assessment and communication of physiologic and behavioral parameters and patterns that assists patients with diabetes with the optimization of their glycemic control. The method and system may use all available sources of information about the patient; (i) EO Data (e.g. self-monitoring of blood glucose (SMBG) and CMG), (ii) Insulin Data (e.g. insulin pump log files or patient treatment records), and (iii) Patient Self Reporting Data (e.g. self treatment behaviors, meals, and exercise) to: retroactively assess the risk of hypoglycemia, retroactively assess risk-based reduction of insulin delivery, and then report to the patient how a risk-based insulin reduction system would have acted consistently to prevent hypoglycemia.

SUMMARY

It is an object of the present disclosure to provide improved technology for automatically detecting a carbohydrate intake event from glucose monitoring data indicative of a glucose level in a system having a data processing device.

For solving the object a method and a system for determining a carbohydrate intake event from glucose monitoring data indicative of a glucose level are provided.

According to an aspect, it is provided a computer-implemented method for determining a carbohydrate intake event from glucose monitoring data indicative of a glucose level in a system having a data processing device provided with one or more processors. A glucose monitoring value is received by the data processing device, the glucose monitoring value indicating a glucose level sampled from a person in a bodily fluid in a glucose level measurement. Insulin bolus administration data indicating an insulin bolus of an insulin bolus administration is received by the data processing device. From an analysis of the glucose monitoring value, by the data processing device, a carbohydrate intake event is detected if one of the following is detected: a) the glucose monitoring value indicates a glucose level below a first threshold glucose level; and b) the glucose monitoring value indicates an elevated glucose level above a second threshold glucose level, and the insulin bolus indicated by the insulin bolus administration data is exceeding a corrective insulin bolus suitable for compensating for the elevated glucose level. Then, the data processing device generates a carbohydrate intake event data indicating the determined carbohydrate intake event.

According to another aspect, it is provided a system comprising a data processing device provided with one or more processors and a display device communicatively coupled to the data processing device. The system is configured to: receive a glucose monitoring value by the data processing device, the glucose monitoring value indicating a glucose level sampled from a person in a bodily fluid in a glucose level measurement; receive, by the data processing device, insulin bolus administration data indicating an insulin bolus of an insulin bolus administration; and determine, by the data processing device, from an analysis of the glucose monitoring value, a carbohydrate intake event if one of the following is detected: a) the glucose monitoring value indicates a glucose level below a first threshold glucose level; and b) the glucose monitoring value indicates an elevated glucose level above a second threshold glucose level, and the insulin bolus indicated by the insulin bolus administration data is exceeding a corrective insulin bolus suitable for compensating for the elevated glucose level. The system is further configured to generate, by the data processing device, carbohydrate intake event data indicating the determined carbohydrate intake event.

Further, a non-transitory computer readable medium is provided.

The method and any further embodiment thereof described herein below can be implemented on any of the systems mentioned below which are preferably adapted to execute these methods.

The management of diabetes is improved, since the diabetes management system can detect if a carbohydrate intake event occurred, e.g. carbohydrate consumption was so far not stored in the diabetes management system although the event is likely to have occurred or will occur as planned by the patient (e.g. the patient administered an insulin bolus in advance of meal he planned to eat soon). Therefore, the system is configured to inform the patient and/or request from the patient, preferably without additional or further user or patient input, to enter such missing carbohydrate intake event data. Event determination may be performed only based on the data (free of additional user/patient input). Such data then allows the system to not only complete the data set on diabetes management relevant data but also improves the ability of the system to provide adequate data on the patient's glycemic/therapeutic status and further enables or improves adequate therapeutic guidance to the patient.

The system may be a diabetes management system which in turn may be (i) a drug infusion system including an infusion pump or infusion pen, preferably for infusion of insulin, (ii) a blood glucose spot measurement system which may in turn may comprise a measurement device with a sensor and a control unit, the latter being either integrated into the measurement device or being a device (such as a remote control or smartphone) separated from but in communication with the measurement device, (iii) a continuous glucose measurement system which may in turn comprise a measurement device with the sensor and a control unit, the latter being either integrated into the measurement device or being a device (such as a remote control or smartphone) separated from but in communication with the measurement device, (iv) a server or remote computer based hardware or software application in communication or at least temporarily connected to any of the aforementioned (i) to (iii) or a part thereof.

The wording "the corrective insulin bolus suitable for compensating for the elevated glucose level" as used here means a bolus that is suitable to change the measured elevated glucose level in the patient such that the glucose level will drop to a target glucose level.

There may be a plurality (i.e. two or more) of glucose monitoring values or data provided by a stream of data collected or sampled in a bodily fluid of a person or patient for at least one sample time over a measurement or monitoring time period in a glucose level monitoring. In case of the plurality glucose monitoring values or data, the following may be provided: determining, by the data processing device, from an analysis of the plurality of glucose monitoring values, a carbohydrate intake event if at least one of the following is detected: a) one or more glucose monitoring values from the plurality of glucose monitoring values indicate a glucose level below a first threshold glucose level; and b) one or more glucose monitoring values from the plurality of glucose monitoring values indicate an elevated glucose level above a second threshold glucose level, and the insulin bolus indicated by the insulin bolus administration data is exceeding a corrective insulin bolus needed for compensating for the elevated glucose level.

The bodily fluid may be blood or interstitial fluid or any other suitable body fluid or body sample. The sample time is a parameter that indicates when, during the measurement or monitoring time period, the respective glucose value is detected in the glucose level measurement.

The at least one of glucose monitoring values may be received from a data storage medium storing the plurality of glucose monitoring values prior to the transmission to the data processing device. As an alternative, the glucose monitoring value(s) may be received from a measurement device directly, such as a biosensor or a glucose measurement system. In one embodiment the received one or more glucose monitoring values are associated with a monitoring time period, preferably a time period of a time window of up to 5 min, up to 10 min, up to 15 min, up to 20 min, up to 25 min, up to 30 min. If at least two glucose monitoring values are used it is possible to calculate a rate of change of the glucose monitoring values and to take this rate of change into account in the determination of a carbohydrate intake event from glucose monitoring data.

The receiving may comprise receiving, by the data processing device, insulin bolus administration data indicating an insulin bolus administration which was administered at a bolus administration time prior to or after the time the glucose monitoring value was measured.

The determining may comprise determining, by the data processing device, from an analysis of the glucose monitoring value, a carbohydrate intake event within a time window of up to +/−30 minutes comprising the bolus administration time, wherein the carbohydrate intake event is determined if one of the following is detected: the glucose monitoring value indicates a glucose level below a first threshold glucose level, and the glucose monitoring value indicates an elevated glucose level above a second threshold glucose level, and, further, the insulin bolus indicated by the insulin bolus administration data is exceeding a corrective insulin bolus suitable for compensating for the elevated glucose level.

The determining may comprise determining, by the data processing device, the corrective insulin bolus suitable for compensating for the elevated glucose level.

The determining may comprise, by the data processing device, determining whether the insulin bolus is exceeding the corrective insulin bolus by at least a predefined factor; and determining, from the analysis of the glucose monitoring value, the carbohydrate intake event if the insulin bolus (which is the actually administered bolus) is exceeding the corrective insulin bolus by at least the predefined factor. The predefined factor may be determined by comparing the corrective insulin bolus value with the insulin bolus. The comparison can mathematically be achieved by subtraction, division, addition or multiplication. Preferably, the predefined factor corresponds to =insulin bolus: corrective insulin bolus. The predefined factor may be more than 1. The predefined factor may be at least 1.1, at least 1.2, at least 1.3, at least 1.4, at least 1.5, at least 1.6 or at least 2. For example, if the factor is 1.1, a carbohydrate intake event is detected when the (administered) insulin bolus exceeds the corrective insulin bolus indicated by the insulin bolus administration data by at least a factor of 1.1. If, for example, an elevated glucose level (above a second threshold glucose level of 160 mg/dL) of 170 g/dL is detected, the corrective insulin bolus is 3 units of insulin and the administered bolus by the patient is 3.6 units, then the administered bolus exceeds the corrective insulin bolus by a factor is 1.2. If in this example the predefined factor is 1.1, the method would then determine a carbohydrate intake event.

In another embodiment, the determining may comprise, by the data processing device, determining a) if the insulin bolus is exceeding the corrective insulin bolus by at least a predefined factor; and b) if the excessive glucose reduction is above a threshold excessive glucose reduction, and determining from the analysis of the at least one glucose monitoring values, the carbohydrate intake event if i) the insulin bolus (which is the actually administered bolus) is exceeding the corrective insulin bolus by at least the predefined factor, and ii) the excessive glucose reduction is above a threshold excessive glucose reduction value. The predefined factor is determined as described above. In one embodiment, the excessive glucose reduction can be calculated based on the corrective insulin bolus value, the actually administered insulin bolus value and the insulin sensitivity. For example the excessive glucose reduction can be calculated as follows: excessive glucose reduction=(corrective insulin bolus value−actually administered insulin bolus value)×insulin sensitivity.

In one embodiment the excessive glucose reduction value is at least 20 mg/dl, preferably at least 30 mg/dl, at least 40 mg/dl, or at least 50 mg/dl.

The threshold excessive glucose reduction value can be predefined, and may be defined by the manufacturer, a third party like a healthcare professional or by the user or patient.

The "insulin sensitivity" means the extent of blood glucose level reduction resulting from the administration of one unit of insulin. The insulin sensitivity may be different from patient to patient and may also change over time in a given patient. For example, the insulin sensitivity may be 10 mg blood glucose/dl blood/unit insulin. The insulin sensitivity is generally determined empirically.

The above corrective insulin bolus can be calculated based on the measured glucose level, the target glucose level and the insulin sensitivity.

The "target glucose level" means a level of glucose in a patient that the insulin therapy is intended to reach or maintain as a result of the insulin administration. For example the insulin therapy could be tailored such that the administered insulin is selected to yield that the measured glucose level in the patient will change to 90 mg/dl (plasma glucose/blood volume). The target glucose level can also be an interval of glucose levels. As the case may be the target glucose level may change depending on the patient or other circumstance. The interval of glucose levels may be 70 to 130 mg/dl before any of breakfast lunch, snack, up to 90 to 180 mg/dl two hours after lunch, 90 to 150 mg/dl at bedtime, etc. The skilled patient or health professional is well aware which target glucose level is appropriate for a given patient and how to tailor the therapy accordingly.

The "carbohydrate factor" also called carb factor, means the amount of insulin needed in a given time interval for a given patient to compensate a certain amount of consumed carbohydrates. The carbohydrate factor may be different from patient to patient and may also change over time in a given patient. The carbohydrate factor also depends on the type of insulin administered. The carbohydrate factor, for example allows calculating the amount of insulin that needs to be administered when the patient consumes a certain amount of carbohydrates. The carbohydrate factor is generally determined empirically.

"Carbohydrate amount" can be indicated in various ways such as in bread units or grams of carbohydrate.

The method may further comprise, by the data processing device, determining the carbohydrate intake event within a time window comprising the bolus administration time.

The insulin bolus administration data indicates an insulin bolus of an insulin bolus administration which was administered within a time period prior to or after the time the glucose monitoring value was measured. The time period may indicate a time period prior to or after the time the last of the at least one glucose monitoring values was measured. For example, a time period or time window of up to +/−5 min, up to +/−10 min, up to +/−15 min, up to +/−20 min, up to +/−25 min, or up to +/−30 min may be applied.

In another embodiment the rate of change of the measured glucose levels is measured and the extent of the rate of change may be taken into account when interpreting a) the at least one glucose monitoring values indicating a glucose level below a first threshold glucose level, or b) the one or more glucose monitoring values from the at least one glucose monitoring value indicating an elevated glucose level above a second threshold glucose level when the insulin bolus indicated by the insulin bolus administration data is exceeding a corrective insulin bolus suitable for compensating for the elevated glucose level. For example such rate-of-change information may indicate a trend of the one or more glucose monitoring values from the at least one glucose monitoring values indicating a glucose level below a first threshold glucose level towards even lower glucose levels; in this situation an administered bolus is plausible, e.g. if a carbohydrate intake event is planned by the patient to occur soon. In another example such rate-of-change information may indicate a trend of the one or more glucose monitoring values from the at least one glucose monitoring value indicating an elevated glucose level above a second threshold, the trend being towards lower glucose levels and the insulin bolus indicated by the insulin bolus administration data is exceeding a corrective insulin bolus suitable for compensating for the elevated glucose level; in this situation an administered bolus is plausible, e.g. if a carbohydrate intake event is planned by the patient to occur soon.

The method may further comprise generating, by the data processing device, data indicative of an amount of carbohydrates associated with the carbohydrate intake event based on the corrective insulin bolus suitable for compensating for the elevated glucose; the insulin bolus indicated by the insulin bolus administration data which exceeds the corrective insulin bolus suitable for compensating for the elevated glucose level; and a carbohydrate factor. For example, if the carbohydrate factor (CF) is 0.1 units of insulin per gram of carbohydrate, the corrective insulin bolus suitable for compensating for the elevated glucose level (CIB) is 2 units, and the administered insulin bolus exceeding a corrective insulin bolus suitable for compensating for the elevated glucose level (AIB) is 5 units, then the carbohydrate intake event corresponds to a carbohydrate amount of: (AIB−CIB)/CF=(5 U−2 U)/0.1 U/gram=30 gram carbohydrate.

The method may further comprise, by the data processing device, generating signal data for signaling at least one the determining of the carbohydrate intake event to the user, and the determining the data on the amount of carbohydrates associated with the carbohydrate intake event; and outputting the signal data through an output device connected to the data processing device. The signal data can be a message, a film, an icon or any other kind of display of information.

The method may further comprise: requesting, by the data processing device, the user to input at least one of carbohydrate event data and confirmation of a carb event; and receiving, by the data processing device, user input indicating at least one of the carbohydrate event data input and the confirmation of the carb event. In one embodiment the data on the amount of carbohydrates is output to the patient as a proposal to specify the amount of carbohydrates underlying the determined carbohydrate intake event which was not so far input into the system. The patient may then be prompted to input acceptance, amendment or rejection of the proposed carbohydrate event data. In the event the proposal is accepted or amended by the patient the data is stored, e.g. in the data processing device as a carbohydrate intake event. Preferably the carbohydrate intake event data comprises at least the amount of carbohydrates and the time of carbohydrate consumption and optionally further comprises at least one of a category of food, an image of the food, and a description of the food.

In one embodiment the user input may be entered after a period of time of up to 2 weeks, up to 1 week, up to 5 days, up to 4 days, up to 3 days, up to 2 days, up to 1 day, up to 18 hours, up to 12 hours, or up to 6 hours, after the time of an insulin bolus administration, e.g. when the carb event log book is analyzed retrospectively.

The receiving of the glucose monitoring value may comprise receiving, by the data processing device, a continuous glucose monitoring value, the continuous glucose monitoring value indicating a glucose level sampled for the person in the bodily fluid in a continuous glucose level measurement. Such measurement can be accomplished, e.g. by using available continuous glucose sensor measurement system such as the Dexcom's G5 sensor. A plurality of continuous glucose monitoring values may be provided. The plurality of continuous glucose monitoring values may be associated with a monitoring time period.

The receiving of the glucose monitoring value may comprise receiving, by the data processing device, a discontinuous glucose monitoring value, the discontinuous glucose monitoring value indicating a glucose level sampled for the person in the bodily fluid in a discontinuous glucose level measurement. A plurality of discontinuous glucose monitoring values may be provided. The plurality of discontinuous glucose monitoring values may be associated with a monitoring time period. Such measurement can be accomplished, e.g. by using available spot blood glucose sensor measurement system such as the Accu-Chek® Aviva, Accu-Chek® Nano.

The carbohydrate intake event may be determined at a time before or after the bolus administration time. In an alternative embodiment, the carbohydrate intake event may be determined at a time before or after the bolus administration time. The time before or after the bolus administration time may be in close vicinity to the carbohydrate intake event time, e.g., within a time window of +/−5 min, +/−10 min, +/−15 min, +/−20 min, +/−25 min, or +/−30 min.

The glucose monitoring data may be analyte monitoring data providing a stream of data collected or sampled for a person or patient for at least one sample time over a measurement time period in an analyte level monitoring, the analyte level being indicative of a glucose level in a bodily fluid.

With regard to a glucose measurement or monitoring, a glucose level or value may be determined by analyzing a blood sample via e.g. spot monitoring, and, as an alternative or in addition, by continuous glucose monitoring (CGM) via a fully or partially implanted sensor. In general, in the context of CGM a glucose value or level in a bodily fluid may be determined. The analyte value may be, e.g., subcutaneously measured in an interstitial fluid. CGM may be implemented as a nearly real-time or quasi-continuous monitoring procedure frequently or automatically providing/updating analyte values without user interaction.

The various embodiments referred to above with regard to a method may apply to the system accordingly.

DESCRIPTION OF FURTHER EMBODIMENTS

Figure 2:
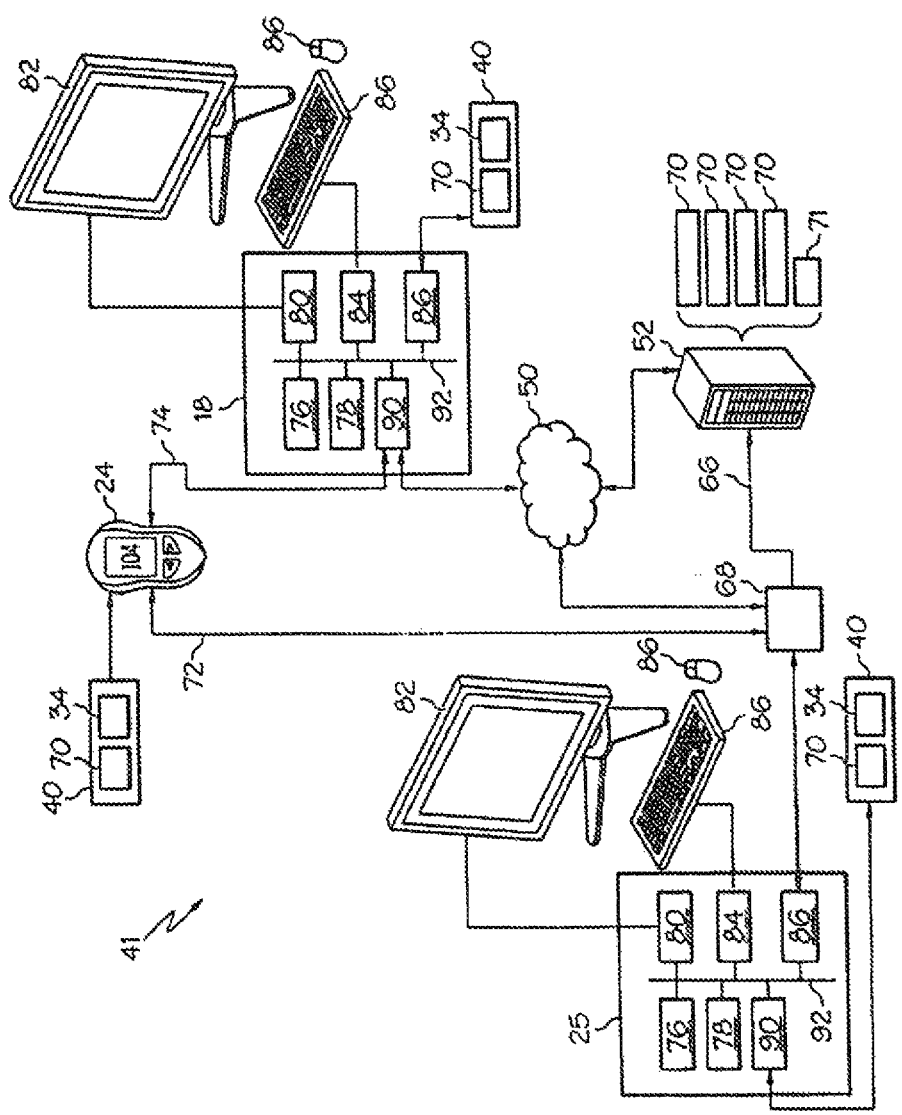
Figure 3:
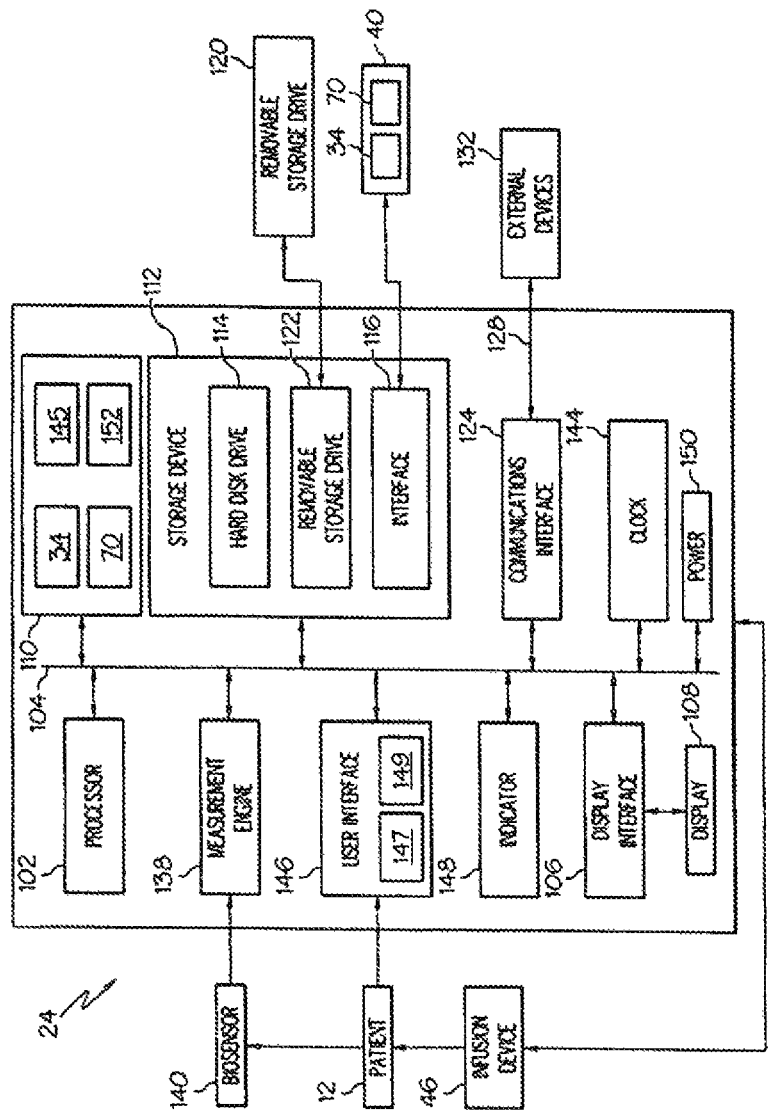
Figure 4:
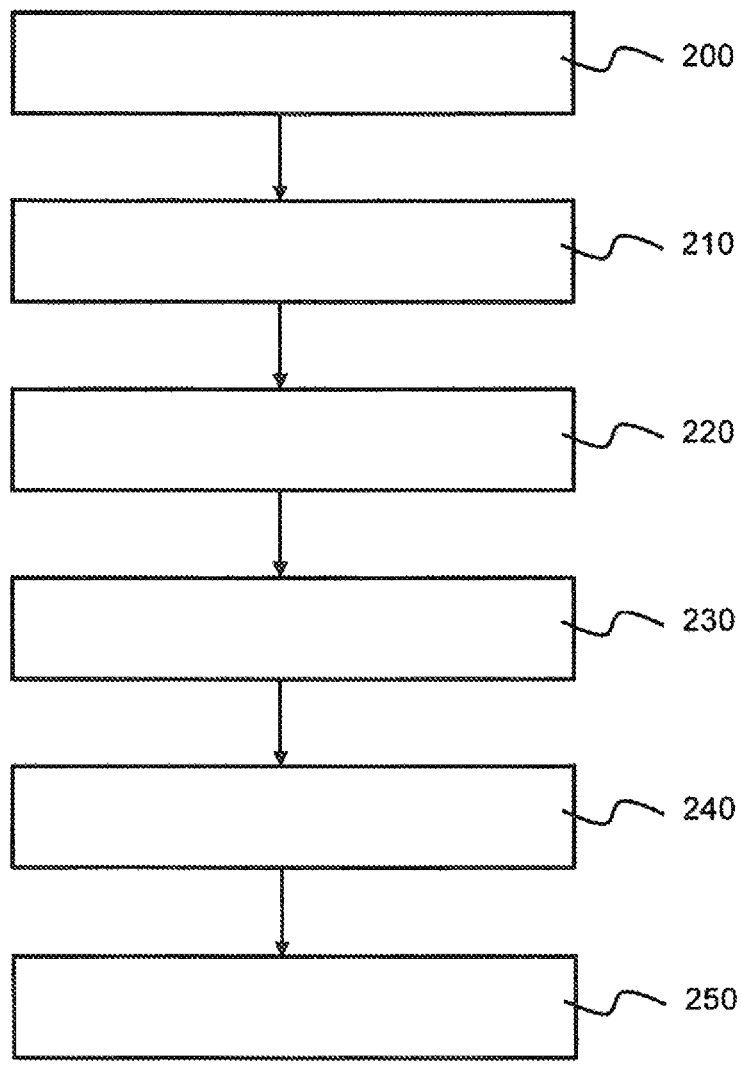

Following, further embodiments are described with a reference to figures. In the figures, show:

FIG. 1 a schematic representation of a diabetes management system for a diabetes patient;

FIG. 2 a schematic representation of a system suitable for implementing a computer-implemented method;

FIG. 3 a schematic representation of a collection device for collecting glucose monitoring data; and FIG. 4 a schematic block diagram of a method for analyzing glucose monitoring data indicative of a glucose level.

FIG. 1 shows a diabetes management system 10 for one or more diabetes patients 12 and a clinician(s) 14 along with others 16 having an interest in the diabetes management of the patient 12.

With regard to alternative embodiments, the diabetes management system 10 may be provided with or as (i) a drug infusion system including an infusion pump or infusion pen, preferably for infusion of insulin, (ii) a blood glucose spot measurement system which may in turn may comprise a measurement device with a sensor and a control unit, the latter being either integrated into the measurement device or being a device (such as a remote control or smartphone) separated from but in communication with the measurement device, (iii) a continuous glucose measurement system which may in turn comprise a measurement device with the sensor and a control unit, the latter being either integrated into the measurement device or being a device (such as a remote control or smartphone) separated from but in communication with the measurement device, (iv) a server or remote computer based hardware or software application in communication or at least temporarily connected to any of the aforementioned (i) to (iii) or a part thereof.

Patient 12, having dysglycemia, may include persons with a metabolic syndrome, prediabetes, type 1 diabetes, type 2 diabetes, and gestational diabetes. The others 16 with an interest in the patient's care may include family members including children or parents, friends, and support groups, all of which can influence the patient's conformance with therapy. The patient 12 may have access to a patient computer 18, such as a home computer, which can connect to a public network 50 (wired or wireless), such as the internet, cellular network, etc., and couple to a dongle, docking station, or device reader 22 for communicating with an external portable device, such as a portable collection device 24 (see FIG. 2). An example of a device reader is shown in the manual "Accu-Chek® Smart Pix Device Reader Users Manual" (2008) available from Roche Diagnostics.

The collection device 24 can be essentially any portable electronic device that can function as an acquisition mechanism for determining and storing digitally glucose value(s), such as a continuous or a discontinuous glucose measurement system. In one embodiment, the collection device 24 can be a blood glucose spot measurement system 26 or a continuous glucose measurement system 28.

In addition to the collection device 24, the patient 12 can use a variety of products to manage his or her diabetes including: test strips 30 carried in a vial 32 for use in the collection device 24; software 34 which can operate on the patient computer 18, the collection device 24, a handheld computing device 36, such as a laptop computer, a personal digital assistant, and/or a mobile phone; and paper tools 38. Software 34 can be pre-loaded or provided either via a computer readable medium 40 or over the public network 50 and loaded for operation on the patient computer 18, the collection device 24, the clinician computer/office workstation 25, and the handheld computing device 36, if desired. In still other embodiments, the software 34 can also be integrated into the device reader 22 that is coupled to the computer (e.g., computers 18 or 25) for operation thereon, or accessed remotely through the public network 50, such as from a server 52.

The patient 12 can also use, for certain diabetes therapies, additional therapy devices 42 and other devices 44. Therapy devices 42 can include devices such as an ambulatory infusion pump 46, an insulin pen 48, and a lancing device 51. An example of an ambulatory insulin pump 46 include but not limited thereto the Accu-Chek® Spirit pump described in the manual "Accu-Chek® Spirit Insulin Pump System Pump User Guide" (2007) available from Roche Diabetes Care. The other devices 44 can be medical devices that provide patient data such as blood pressure, fitness devices that provide patient data such as exercise information, and elder care device that provide notification to care givers. The other devices 44 can be configured to communicate with each other according to standards planned by Continua® Health Alliance.

The clinicians 14 for diabetes are diverse and can include, for example, nurses, nurse practitioners, physicians, endocrinologists, and other such health care providers. The clinician 14 typically has access to a clinician computer 25, such as a clinician office computer, which can also be pro-vided with the software 34. A healthcare record system 27, such as Microsoft® Health Vault™ and Google™ Health, may also be used by the patient 12 and the clinician 14 on computers 18, 25 to exchange information via the public network 50 or via other network means (LANs, WANs, VPNs, etc.), and to store information such as collection data from the collection device 24 to an electronic medical record of the patient e.g., EMR which can be provided to and from computer 18, 25 and/or server 52.

Most patients 12 and clinicians 14 can interact over the public network 50 with each other and with others having computers/servers 52. Such others can include the patient's employer 54, a third party payer 56, such as an insurance company who pays some or all of the patient's healthcare expenses, a pharmacy 58 that dispenses certain diabetic consumable items, a hospital 60, a government agency 62, which can also be a payer, and companies 64 providing healthcare products and services for detection, prevention, diagnosis and treatment of diseases. The patient 12 can also grant permissions to access the patient's electronic health record to others, such as the employer 54, the payer 56, the pharmacy 58, the hospital 60, and the government agencies 62 via the healthcare record system 27, which can reside on the clinician computer 25 and/or one or more servers 52. Reference hereafter is also made to FIG. 2.

FIG. 2 shows a system 41 suitable for implementing embodiments described herein, which in another embodiment can be a part of the diabetes management system 10 and communicate with such components, via conventional wired or wireless communication means. As an alternative, only selected elements of the system 41 may be provided for implementing the technologies described herein. For example, analyzing and visualizing of the glucose values may be done in the collection device 24 and/or some of the data processing devices (computer) communicatively connected to the collection device 24.

The system 41 can include the clinician computer 25 that is in communication with a server 52 as well as the collection device 24. Communications between the clinician computer 25 and the server 52 can be facilitated via a communication link to the public network 50, to a private network 66, or combinations thereof. The private network 66 can be a local area network or a wide are network (wired or wireless) connecting to the public network 50 via a network device 68 such as a (web) server, router, modem, hub, and the like.

In one embodiment, the server 52, as well as the network device 68, can function also as a data aggregator for collected glucose monitoring data 70. Accordingly, in such an embodiment, the glucose monitoring data 70 of a completed collection procedure(s) from a collection device of the patient 12 can then be provided from the server 52 and/or network device 68 to the clinician computer 25 when requested in response to a retrieval for such patient data.

In one embodiment, one or more of a plurality of instances of glucose monitoring data 70 aggregated on the server 52 can be provided over the public network 50, such as through a secure web interface implemented on the patient computer 18, the clinician computer 25, and/or the collection device 24. In another embodiment, the clinician computer 25 can serve as the interface (wired or wireless) 72 between the server 52 and the collection device 24. In still another embodiment, glucose monitoring data 70, as well as software 34, may be provided on a computer readable medium 40 and loaded directly on the patient computer 18, the clinician computer 25, and/or the collection device 24. In still another embodiment, glucose monitoring data 70 and software 34 may be sent between the patient computer 18, the clinician computer 25, the server 52 and/or the collection device 24 via the public network 50, the private network 66, via a direct device connection (wired or wireless) 74, or combinations thereof. Accordingly, in one embodiment the external devices e.g., computer 18 and 25, can be used to establish a communication link 72, 74 between the collection device 24 and still further electronic devices such as other remote Personal Computer (PC), and/or servers such as through the public network 50, such as the Internet and/or other communication networks (e.g., LANs, WANs, VPNs, etc.), such as private network 66.

The patient computer 18, as a conventional personal computer/workstation, can include a processor 76 which executes programs, such as software 34, and such as from memory 78 and/or computer readable medium 40. Memory 78 can include system memory (RAM, ROM, EEPROM, etc.), and storage memory, such as hard drives and/or flash memory (internal or external). The patient computer 18 can also include a graphics processor 80 (e.g., to interface a display 82 with the processor 76, input/output connections 84 for connecting user interface devices 86, such as a keyboard and mouse (wired or wireless), and computer readable drives 88 for portable memory and discs, such as computer readable medium 40. The patient computer 18 can further include communication interfaces 90 for connections to the public network 50 and other devices, such as collection device 24 (wired or wireless), and a bus interface 92 for connecting the above mentioned electronic components to the processor 76.

Similarly, the clinician computer 25, as a conventional personal computer/workstation, can include a processor 76 which executes programs, such as software 34, and such as from memory 78 and/or computer readable medium 40. The clinician computer 25 can also include a graphics processor 80 to interface a display 82 with the processor 76, input/output connections 84 for connecting user interface devices 86, such as a keyboard and mouse (wired or wireless), and computer readable drives 88 for portable memory and discs, such as computer readable medium 40. The clinician computer 25 can further include communication interfaces 90 for connections to the public network 50 and other devices, such as collection device 24 (wired or wireless), and a bus interface 92 for connecting the above mentioned electronic components to the processor 76. Reference hereafter is now made to FIG. 3.

FIG. 3 is a block diagram schematically illustrating the portable collection device 24 depicted in FIG. 2. In the illustrated embodiment, the collection device 24 can include one or more microprocessors, such as processor 102, which may be a central processing unit comprising at least one or more single or multicore and cache memory, which can be connected to a bus 104, which may include data, memory, control and/or address buses. The collection device 24 can include the software 34, which provides instruction codes that causes a processor 102 of the device to implement the methods provided herein. The collection device 24 may include a display interface 106 providing graphics, text, and other data from the bus 104 (or from a frame buffer not shown) for display on a display 108. The display interface 106 may be a display driver of an integrated graphics solution that utilizes a portion of main memory 110 of the collection device 24, such as random access memory (RAM) and processing from the processor 102 or may be a dedicated graphic processing unit. In an-other embodiment, the display interface 106 and display 108 can additionally provide a touch screen interface for providing data to the collection device 24 in a well-known manner.

Main memory 110 in one embodiment can be random access memory (RAM), and in other embodiments may include other memory such as a ROM, PROM, EPROM or EEPROM, and combinations thereof. In one embodiment, the collection device 24 can include secondary memory 112, which may include, for example, a hard disk drive 114 and/or a computer readable medium drive 116 for the computer readable medium 40, representing for example, at least one of a floppy disk drive, a magnetic tape drive, an optical disk drive, a flash memory connector (e.g., USB connector, Firewire connector, PC card slot), etc. The drive 116 reads from and/or writes to the computer readable medium 40 in a well-known manner. Computer readable medium 40, represents a floppy disk, magnetic tape, optical disk (CD or DVD), flash drive, PC card, etc. which is read by and written to by the drive 116. As will be appreciated, the computer readable medium 40 can have stored therein the software 34 and/or glucose monitoring data 70 resulting from completed collections performed according to one or more of the collection procedures.

In alternative embodiments, secondary memory 112 may include other means for allowing the software 34, other computer programs or other instructions to be loaded into the collection device 24. Such means may include, for example, a removable storage unit 120 and an interface connector 122. Examples of such removable storage units/interfaces can include a program cartridge and cartridge interface, a removable memory chip (e.g., ROM, PROM, EPROM, EEPROM, etc.) and associated socket, and other removable storage units 120 (e.g. hard drives) and interface connector 122 which allow software and data to be transferred from the removable storage unit 120 to the collection device 24.

The collection device 24 in one embodiment can include a communication module 124 which may comprise a transceiver module. The communication module 124 allows software and data (e.g., glucose monitoring data 70 resulting from completed collections) to be transferred between the collection device 24 and an external device(s) 126. Further examples of communication module 124 may include one or more of a modem, a network interface (such as an Ethernet card), a communications port (e.g., USB, Firewire, serial, parallel, etc.), a PC or PCMCIA slot and card, a wireless transceiver, and combinations thereof.

The external device 126 can be the patient computer 18, the clinician computer 25, the handheld computing devices 36, such as a laptop computer, a personal digital assistance (PDA), a mobile (cellular) phone, and/or a dongle, a docking station, or device reader 22. In such an embodiment, the external device 126 may provide and/or connect to one or more of a modem, a network interface (such as an Ethernet card), a communications port (e.g., USB, Firewire, serial, parallel, etc.), a PCMCIA slot and card, a wireless transceiver, and combinations thereof for providing communication over the public network 50 or private network, such as with the clinician computer 25 or server 52.

Software and data transferred via communication module 124 can be in the form of wired or wireless signals 128, which may be electronic, electromagnetic, optical, or other signals capable of being sent and received by communication module 124. For example, as is known, signals 128 maybe sent between communication module 124 and the external device(s) 126 using wire or cable, fiber optics, a phone line, a cellular phone link, an RF link, an infrared link, other communications channels, and combinations thereof. Specific techniques for connecting electronic devices through wired and/or wireless connections (e.g. USB and Bluetooth, respectively) are well known in the art.

In another embodiment, the collection device 24 can be used with the external device 132, such as provided as a handheld computer or a mobile phone, to perform actions such as prompt a patient to take an action, acquire a data event, and perform calculations on information.

In the illustrative embodiment, the collection device 24 can provide a measurement engine 138 for reading a biosensor 140. The biosensor 140, which in one embodiment is the disposable test strip 30 (FIG. 1), is used with the collection device 24 to receive a sample such as for example, of capillary blood, which is exposed to an enzymatic reaction and measured by electrochemistry techniques, optical techniques, or both by the measurement engine 138 to measure and provide a glucose monitoring value, such as for example, a blood glucose level. In other embodiments, the measurement engine 138 and biosensor 140 can be of a type used to provide a glucose monitoring value for other types of sampled fluids or analytes besides or in addition to glucose, heart rate, blood pressure measurement, and combinations thereof. Such an alternative embodiment is useful in embodiments where values from more than one glucose monitoring type are requested by a structured collection procedure. In still another embodiment, the biosensor 140 may be a sensor with an indwelling catheter(s) or being a subcutaneous tissue fluid sampling device(s), such as when the collection device 24 is implemented as a continuous glucose monitor (CGM), optionally in communication with an infusion device, such as insulin pump 46 (FIG. 1). In alternative embodiments, the collection device 24 can be a controller implementing the software 34 and communicating between the infusion device (e.g., ambulatory insulin pump 46 and electronic insulin pen 48) and the biosensor 140.

Data, comprising at least the information collected by the biosensor 140, is provided by the measurement engine 138 to the processor 102 which may execute a computer program stored in memory 110 to perform various calculations and processes using the data. The data from the measurement engine 138 and the results of the calculation and processes by the processor 102 using the data is herein referred to as self-monitored data. The self-monitored data may include, but not limited thereto, the glucose values of a patient 12, the insulin dose values, the insulin types, and the parameter values used by processor 102 to calculate future glucose values, supplemental insulin doses, and carbohydrate supplement amounts as well as such values, doses, and amounts. Such data along with a date-time stamp for, e.g., each measured glucose value and optionally each administered insulin dose value is stored in a data file 145 of memory 110 and/or 112. An internal clock 144 of the collection device 24 can supply the current date and time to processor 102 for such use.

The collection device 24 can further provide a user interface 146, such as buttons, keys, a trackball, touchpad, touch screen, etc. for data entry, program control and navigation of selections, choices and data, making information requests, and the like. In one embodiment, the user interface 146 can comprises one or more buttons 147, 149 for entry and navigation of the data provided in memory 110 and/or 112. In one embodiment, the user can use one or more of buttons 147, 149 to enter (document) contextualizing information, such as data related to the everyday lifestyle of the patient 12 and to acknowledge that prescribed tasks are completed. Such lifestyle data may relate to carbohydrate intake events such as food intake, insulin bolus, insulin basal rates or regimen, medication use, energy levels, exercise, sleep, general health conditions and overall well-being sense of the patient 12 (e.g., happy, sad, rested, stressed, tired, etc.). Such lifestyle data can be recorded into memory 110 and/or 112 of the collection device 24 as part of the self-monitored data via navigating through a selection menu displayed on display 108 using buttons 147, 149 and/or via a touch screen user interface provided by the display 108. It is to be appreciated that the user interface 146 can also be used to display on the display 108 the self monitored data or portions thereof, such as used by the processor 102 to display measured glucose levels as well as any entered data. The user interface 146 provided with some or all the elements described above may be used in the method for determining a carbohydrate intake event from glucose monitoring data indicative of a glucose level as described with reference to FIG. 4 below.

The user interface 146 may be used for outputting data indicative of an amount of carbohydrates associated with a carbohydrate intake event based on a corrective insulin bolus suitable for compensating for an elevated glucose level. In addition or as an alternative, data indicative of one of an insulin bolus indicated by insulin bolus administration data which exceeds the corrective insulin bolus suitable for compensating for the elevated glucose level, and a carbohydrate factor may be outputted via the user interface 146. For example, the carbohydrate intake event corresponds to a carbohydrate amount of (AIB−CIB)/CF=(5 U−2 U)/0.1 U/gram=30 gram carbohydrate, if the following is provided: the carbohydrate factor (CF) is 0.1 units of insulin per gram of carbohydrate; the corrective insulin bolus suitable for compensating for the elevated glucose level (CIB) is 2 units; and the administered insulin bolus exceeding a corrective insulin bolus suitable for compensating for the elevated glucose level (AIB) is 5 units.

In one embodiment, the collection device 24 can be switched on by pressing any one of the buttons 147, 149 or any combination thereof. In another embodiment, in which the biosensor 140 is a test-strip, the collection device 24 can be automatically switched on when the test-strip is inserted into the collection device 24 for measurement by the measurement engine 138 of a glucose level in a sample of blood placed on the test-strip. In one embodiment, the collection device 24 can be switched off by holding down one of the buttons 147, 149 for a pre-defined period of time, or in another embodiment can be shut down automatically after a pre-defined period of non-use of the user interface 146.

An indicator 148 can also be connected to processor 102, and which can operate under the control of processor 102 to emit audible, tactile (vibrations), and/or visual alerts/reminders to the patient of daily times for bG measurements (bG—blood glucose) and events, such as for example, to take a meal, of possible future hypoglycemia, and the like. A suitable power supply 150 is also provided to power the collection device 24 as is well known to make the device portable.

As mentioned above previously, the collection device 24 may be pre-loaded with the software 34 or be provided therewith via the computer readable medium 40 as well as received via the communication module 124 by signal 128 directly or indirectly though the external device 132 and/or network 50. When provided in the latter matter, the software 34 when received by the processor 102 of the collection device 24 is stored in main memory 110 (as illustrated) and/or secondary memory 112. The software 34 contains instructions, when executed by the processor 102, enables the processor to perform the features/functions as discussed herein. In another embodiment, the software 34 may be stored in the computer readable medium 40 and loaded by the processor 102 into cache memory to cause the processor 102 to perform the features/functions as described herein. In another embodiment, the software 34 is implemented primarily in hardware logic using, for example, hardware components such as application specific integrated circuits (ASICs). Implementation of the hardware state machine to perform the feature/functions described herein will be apparent to persons skilled in the relevant art(s). In yet another embodiment, the technology is implemented using a combination of both hardware and software.

It is to be appreciated that glucose monitoring data 70, which can include or be associated with self-monitored data and/or contextual information can be sent/downloaded (wired or wireless) from the collection device 24 via the communication module 124 to another electronic device, such as the external device 132 (PC, PDA, or cellular telephone), or via the network 50 to the clinician computer 25. Clinicians can use diabetes software provided on the clinician computer 25 to evaluate the received glucose monitoring data 70 of the patient 12 for therapy results.

In one embodiment, the collection device 24 can be provided as portable blood glucose meter, which is used by the patient 12 for recording self-monitored data comprising insulin dosage readings and spot measured glucose levels. Accordingly, it is to be appreciated that the collection device 24 can include the software and hardware necessary to process, analyze and interpret the self monitored data in accordance with predefined flow sequences (as described below in detail) and generate an appropriate data interpretation output. In one embodiment, the results of the data analysis and interpretation performed upon the stored patient data by the collection device 24 can be displayed in the form of a report, trend-monitoring graphs, and charts to help patients manage their physiological condition and support patient-doctor communications. In other embodiments, the bG data from the collection device 24 may be used to generate reports (hardcopy or electronic) via the external device 132 and/or the patient computer 18 and/or the clinician computer 25.

The collection device 24 can further provide the user and/or his or her clinician with at least one or more of the possibilities comprising: a) editing data descriptions, e.g. the title and description of a record; b) saving records at a specified location, in particular in user-definable directories as described above; c) recalling records for display; d) searching records according to different criteria (date, time, title, description etc.); e) sorting records according to different criteria (e.g., values of the bG level, date, time, duration, title, description, etc.); f) deleting records; g) exporting records; and/or h) performing data comparisons, modifying records, excluding records as is well known.

In still another embodiment, the software 34 can be implemented on the continuous glucose monitor 28 (FIG. 1). In this manner, the continuous glucose monitor 28 can be used to obtain time-resolved data. Such time-resolved data can be useful to identify fluctuations and trends that would otherwise go unnoticed with spot monitoring of blood glucose levels and standard HbA1c tests. Such as, for example, low overnight glucose levels, high blood glucose levels between meals, and early morning spikes in blood glucose levels as well as how diet and physical activity affect blood glucose along with the effect of therapy changes.

In addition to collection device 24, clinicians 14 can prescribe other diabetes therapy devices for patients 12 such as an ambulatory insulin pump 46 as well as electronically based insulin pen 48 (FIG. 1). The insulin pump 46 can record and provide insulin dosage and other information, as well as the electronically based insulin pen 48, to a computer, and thus can be used as another means for providing glucose monitoring data.

It is to be appreciated that embodiments of the computer-implemented method described hereinafter can be implemented electronically on system 41 (FIG. 2), patient computer 18, clinician computer 25, collection device 24 or on any electronic device/computer that includes a display. Specifically, when the computer-implemented method is executed as a program, i.e., software 34, instructions codes of the program can be executed by one or more processors (e.g., processor 76, processor 102, graphics processor 80, and/or display interface 106) to perform the processes associated therewith. In still other embodiments, some or all of the processes of the software 34 discussed hereafter provided on a non-transient computer readable medium 40 storing program instruction codes that, when executed by one or more processors, causes at least a display communicatively coupled to the one or more processors to perform the processes associated therewith.

FIG. 4 shows a schematic representation of a block diagram with regard to a method for determining a carbohydrate intake event from glucose monitoring data indicative of a glucose level in the system for which alternative embodiments are described above. Continuous and/or discontinuous glucose monitoring data may be analyzed.

In step 200, one or more glucose monitoring values are received in a data processing device having one or more processors. For example a plurality of glucose monitoring values assigned to a monitoring time period may be received. In an alternative, a single glucose monitoring value is received. The data processing device, for example, may be provided on system 41 (FIG. 2), patient computer 18, clinician computer 25, collection device 24 or on any electronic device/computer that optionally includes a display. The glucose monitoring values or data are indicating a glucose level for a person, e.g., the patient 12, in a bodily fluid over a monitoring time period in a continuous and/or discontinuous glucose level measurement.

Further, in step 210 insulin bolus administration data are received by the data processing device. The insulin bolus administration data are indicating an insulin bolus to be administered in an insulin bolus administration. The insulin bolus identified by the insulin bolus administration data may be administered by the ambulatory insulin pump 46. The insulin bolus administration data may be part of administration data assigned to the patient 12 for managing insulin administration. The insulin bolus administration data may provide for automatic control of the insulin administration device, such as the ambulatory insulin pump 46.

In an alternative embodiment, the insulin bolus administration data may comprise additional information. For example, a bolus time may be provided, the bolus time defining a point in time at which the insulin bolus is to be administered.

In step 220, a carbohydrate intake event is determined from an analysis of at least one glucose monitoring value by the data processing device. Start of the determination of the carbohydrate intake event may be triggered by detecting or determining one or more criteria or parameters for the at least one glucose monitoring value. According to an embodiment, the carbohydrate intake event may be determined if one or more glucose monitoring values are this in a target range of the glucose value. The target range may be defined prior to the analysis for determining the carbohydrate intake event, e.g., by user input. Information from glucose monitoring processes in the past may be used for determining the target range.

As an alternative or in addition, the carbohydrate intake event may be determined in response to detecting, by the data processing device, one or more glucose monitoring values indicating a glucose level below a first threshold glucose level. Again, the first threshold glucose value may be determined prior to the analysis of the plurality of glucose monitoring values. For example, a user input may be received in the data processing device, the user input defining the first threshold glucose level.

In another alternative embodiment or in addition, the carbohydrate intake event may be detected if one or more glucose monitoring values are indicating an elevated glucose level above the second threshold glucose level, and, further, the insulin bolus indicated by the insulin bolus administration data is exceeding a corrective insulin bolus needed for compensating the elevated glucose level. The insulin bolus being greater than the corrective insulin bolus needed for compensation is taken as an indication for the carbohydrate intake event which in turn has caused a lower glucose level of the patient. Therefore, the insulin bolus originally being defined to be administrated is too high. Only the corrective insulin bolus is necessary for compensating the elevated glucose level presently detected. The threshold criteria or parameter may be defined with regard to determining the carbohydrate intake event from the difference between the insulin bolus indicated by the insulin bolus administration data and the corrective insulin bolus. For example, the insulin bolus may be required to be twice as high (factor 2) as the corrective insulin bolus for determining the carbohydrate intake event.

The corrective insulin bolus may be determined, by the data processing device, taking into account the elevated glucose level and a target glucose level which may be, for example, the second threshold glucose level.

Referring to step 230 in FIG. 4, carbohydrate intake event data are generated by the data processing device, the carbohydrate intake data indicating the determined carbohydrate intake event. As an option, in step 240 signal data may be generated for signaling the determination of the carbohydrate intake event, for example, through to the user interface 146 and components connected to it, such as the display 108. The signaling data may comprise at least one of audio data and video data. By means of the user interface 146 and components connected to it the user may be asked for a response (user input) to the information about the carbohydrate intake event. A user input may be received through the user interface 146, the user input confirming, rejecting or amending the carbohydrate intake event data. Data indicative of the user input may be stored in the system's memory.

Further, the data outputted to the user may indicate an amount of carbohydrates associated with the carbohydrate intake event. The user may be asked for a further user input in response to such data outputted through the user interface 146 and components connected to it. For example, the carbohydrate intake event may correspond to a carbohydrate amount of (AIB−CIB)/CF=(5 U−2 U)/0.1 U/gram=30 gram carbohydrate, if the following is provided: the carbohydrate factor (CF) is 0.1 units of insulin per gram of carbohydrate; the corrective insulin bolus suitable for compensating for the elevated glucose level (CIB) is 2 units; and the administered insulin bolus exceeding a corrective insulin bolus suitable for compensating for the elevated glucose level (AIB) is 5 units.

The further user input may be confirming, rejecting or amending the amount of carbohydrates. Data indicative of the further user input, e.g. an amended amount of carbohydrates, may be stored in the system's memory. In the memory, such data indicative of the further user input may be assigned to the data indicative of the respective carbohydrate intake event determined from the analysis as described above.

In addition or as an alternative, in response to the data output provided through the user interface 146 and components connected to it, supplementary data may be received by user input. The user input may be received in response to a request for supplementary data input outputted through the user interface 146 and components connected to it. The supplementary data, for example, may refer to personal data of the user, such as age or body weight.

As a further option, in step 250 the corrective insulin bolus may be provided to the ambulatory insulin pump 46 for controlling insulin administration.

The invention claimed is:

1. A computer-implemented method for operating a glucose monitoring system in response to the determination of an occurrence of a carbohydrate intake event, the glucose monitoring system having a data processing device provided with one or more processors, the method comprising:
receiving, by the data processing device, insulin bolus administration data indicating an insulin bolus of an insulin bolus administration at a bolus administration time;
conducting a glucose level measurement using a glucose measurement system to obtain a glucose monitoring value of a person;
the glucose monitoring value indicating a glucose level sampled from the person in a bodily fluid, the glucose level being sampled at a time up to 30 minutes before or after the bolus administration time;
providing the glucose monitoring value to the data processing device ;
receiving the glucose monitoring value by the data processing device;
determining by the data processing device a corrective insulin bolus suitable for compensating for an elevated glucose level;
determining, by the data processing device, from an analysis of the glucose monitoring value, the occurrence of a carbohydrate intake event occurring within a time window of up to +/−30 minutes of the bolus administration time, wherein the occurrence of a carbohydrate intake event is determined if one of the following is detected:
the glucose monitoring value indicates a glucose level below a first threshold glucose level; or
the glucose monitoring value indicates an elevated glucose level above a second threshold glucose level, and further, the insulin bolus indicated by the insulin bolus administration data is exceeding the corrective insulin bolus suitable for compensating for the elevated glucose level; and
generating, by the data processing device, carbohydrate intake event data indicating the occurrence of the carbohydrate intake event: and
controlling insulin administration by an ambulatory insulin pump based on the corrective insulin bolus and/or based on the determining of a carbohydrate event.

2. The method according to claim 1, wherein the determining comprises, by the data processing device, determining, from the analysis of the glucose monitoring value, the occurrence of the carbohydrate intake event if the insulin bolus exceeds the corrective insulin bolus by at least a predefined factor.

3. The method according to claim 1, wherein the insulin bolus administration data indicates the insulin bolus of the insulin bolus administration was administered within a time period of up to 30 minutes prior to or after the time the glucose monitoring value was measured.

4. The method according to claim 1, further comprising generating, by the data processing device, data indicative of an amount of carbohydrates associated with the carbohydrate intake event based on:
the corrective insulin bolus suitable for compensating for the elevated glucose;

the insulin bolus indicated by the insulin bolus administration data which exceeds the corrective insulin bolus suitable for compensating for the elevated glucose level; and the amount of insulin needed for the patient to compensate the amount of consumed carbohydrates.

5. The method according to claim 1, further comprising, by the data processing device generating signal data from the generated carbohydrate intake event data for signaling at least one of (a) the determination of the carbohydrate intake event to the user, and (b) the determination of data on an amount of carbohydrates associated with the carbohydrate intake event; and outputting the signal data through an output device connected to the data processing device.

6. The method according to claim 1, further comprising the data processing device requesting the user to input at least one of carbohydrate event data and confirmation of a carb event; and the data processing device receiving user input indicating at least one of the carbohydrate event data input and the confirmation of the carb event.

7. The method according to claim 1, wherein the conducting a glucose level measurement is performed using a continuous glucose monitoring system, the glucose monitoring value indicating a glucose level sampled for the person in the bodily fluid in a continuous glucose level measurement.

8. The method according to claim 1, wherein the conducting a glucose level measurement is performed using a discontinuous glucose measurement system, the glucose monitoring value indicating a glucose level sampled for the person in the bodily fluid in a discontinuous glucose level measurement.

9. The method according to claim 1, wherein the occurrence of the carbohydrate intake event is determined at a time before or after the bolus administration time.

10. The method of claim 1 comprising controlling insulin administration based on the corrective insulin bolus.

11. The method of claim 1 comprising controlling insulin administration based on the determining of a carbohydrate intake event.

12. A system comprising:

a glucose measurement system configured for conducting a glucose level measurement to obtain a glucose monitoring value for a person;

a data processing device provided with one or more processors; and a display device communicatively coupled to the data processing device, the data processing device configured to receive the glucose monitoring value indicating a glucose level sampled at a glucose sampling time from the person in a bodily fluid;

the data processing device further configured to:

receive insulin bolus administration data indicating an insulin bolus administration at a bolus administration time, the glucose sampling time being within 30 minutes of the bolus event, determine a corrective insulin bolus suitable for compensating for an elevated glucose level, and determine from an analysis of the glucose monitoring value, the occurrence of a carbohydrate intake event within a time window of up to +/−30 minutes of the bolus administration time, wherein the occurrence of a carbohydrate intake event is determined if one of the following is detected:

the glucose monitoring value indicates a glucose level below a first threshold glucose level; or the glucose monitoring value indicates an elevated glucose level above a second threshold glucose level, and, further, the insulin bolus indicated by the insulin bolus administration data is exceeding the corrective insulin bolus suitable for compensating for the elevated glucose level;

generate, by the data processing device, carbohydrate intake event data indicating the determined carbohydrate intake event; and control insulin administration by an ambulatory insulin pump based on the corrective insulin bolus and/or based on the determining of a carbohydrate event.

13. The system of claim 12 in which the glucose measurement system is a continuous glucose monitoring system.

14. The system of claim 12 in which the glucose measurement system is a discontinuous glucose measurement system.

15. A non-transitory computer readable medium storing a program causing, when loaded to a data processing device having one or more processors, the data processing device to:

receive a glucose monitoring value indicating a glucose level sampled at a glucose sampling time from a person in a bodily fluid in a glucose level measurement;

receive insulin bolus administration data indicating an insulin bolus administration at a bolus administration time, the glucose sampling time being within 30 minutes of the bolus event, determine a corrective insulin bolus suitable for compensating for an elevated glucose level, determine from an analysis of the glucose monitoring value, the occurrence of a carbohydrate intake event within a time window of up to +/−30 minutes of the bolus administration time, wherein the occurrence of a carbohydrate intake event is determined if one of the following is detected:

the glucose monitoring value indicates a glucose level below a first threshold glucose level; or the glucose monitoring value indicates an elevated glucose level above a second threshold glucose level, and, further, the insulin bolus indicated by the insulin bolus administration data is exceeding a corrective insulin bolus suitable for compensating for the elevated glucose level;

generate carbohydrate intake event data indicating the determined carbohydrate intake event, and control insulin administration by an ambulatory insulin pump based on the corrective insulin bolus and/or based on the determining of a carbohydrate event.

* * * * *